(12) United States Patent
Nagasaka et al.

(10) Patent No.: US 9,566,229 B2
(45) Date of Patent: *Feb. 14, 2017

(54) LIQUID COSMETIC

(75) Inventors: Yuya Nagasaka, Fujioka (JP); Hiroshi Sato, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/805,410

(22) PCT Filed: Jul. 12, 2010

(86) PCT No.: PCT/JP2010/061788
§ 371 (c)(1),
(2), (4) Date: Dec. 19, 2012

(87) PCT Pub. No.: WO2012/008009
PCT Pub. Date: Jan. 19, 2012

(65) Prior Publication Data
US 2013/0101538 A1    Apr. 25, 2013

(51) Int. Cl.
*A61K 8/81* (2006.01)
*A61Q 1/10* (2006.01)
(Continued)

(52) U.S. Cl.
CPC ............. *A61K 8/8182* (2013.01); *A61K 8/19* (2013.01); *A61K 8/8135* (2013.01);
(Continued)

(58) Field of Classification Search
None
See application file for complete search history.

(56) References Cited

U.S. PATENT DOCUMENTS 5,733,344 A    3/1998   Shiraishi et al.
5,830,485 A *  11/1998  Gueret et al. ............... 424/401
(Continued)

FOREIGN PATENT DOCUMENTS

EP     1 977 733 A1    10/2008
EP     1977733 A1 *    10/2008
(Continued)

OTHER PUBLICATIONS

International Search Report (PCT/ISA/210) issued on Oct. 12, 2010, by the Japanese Patent Office as the International Searching Authority for International Application No. PCT/JP2010/061788.
(Continued)

*Primary Examiner* — Bethany Barham
*Assistant Examiner* — Dominic Lazaro
(74) *Attorney, Agent, or Firm* — Buchanan, Ingersoll & Rooney PC

(57) ABSTRACT

Provided is a liquid cosmetic which can suitably be used for a liquid cosmetic applicator using a brush or a pen feed as an applying means and which has good water resistance and is excellent in an adhesive property to the skin. The liquid cosmetic comprises at least carbon black, water, 0.5 to 5% by mass of a dispersant comprising a film-formable resin, 2 to 15% by mass (in terms of a solid content) of a film-forming agent and 0.5% by mass or less of a surfactant, and a viscosity thereof measured at a temperature of 25° C. and a shear rate of 3.83 $S^{-1}$ by means of an ELD type viscometer falls in a range of 2 to 8 mPa·s.

2 Claims, 2 Drawing Sheets

(51) Int. Cl.
*A61K 8/19* (2006.01)
*A45D 34/04* (2006.01)
*A61Q 1/04* (2006.01)

(52) U.S. Cl.
CPC .......... *A61K 8/8147* (2013.01); *A61K 8/8152* (2013.01); *A61K 8/8158* (2013.01); *A61K 8/8176* (2013.01); *A61Q 1/10* (2013.01); *A45D 34/042* (2013.01); *A61K 2800/872* (2013.01); *A61Q 1/04* (2013.01)

(56) References Cited

U.S. PATENT DOCUMENTS

| | | | |
|---|---|---|---|
| 6,534,047 | B1* | 3/2003 | Bodelin ............ 424/70.7 |
| 8,828,369 | B2 | 9/2014 | Morita et al. |
| 2005/0002881 | A1* | 1/2005 | Aota .................. 424/63 |
| 2005/0163741 | A1* | 7/2005 | Zech ................ 424/70.16 |
| 2007/0212316 | A1* | 9/2007 | Feng et al. ............ 424/70.7 |
| 2008/0102047 | A1* | 5/2008 | Appel et al. ............ 424/63 |
| 2009/0116895 | A1* | 5/2009 | Uehara et al. ........... 401/269 |
| 2009/0175813 | A1 | 7/2009 | Morita et al. |
| 2010/0221204 | A1 | 9/2010 | Morita et al. |

FOREIGN PATENT DOCUMENTS

| | | |
|---|---|---|
| FR | 2818900 A1 | 7/2002 |
| JP | 62-226915 A | 10/1987 |
| JP | 63-287712 A | 11/1988 |
| JP | 63-307809 A | 12/1988 |
| JP | 8-157329 A | 6/1996 |
| JP | 9-208436 A | 8/1997 |
| JP | 10-231233 A | 9/1998 |
| JP | 2000-247833 A | 9/2000 |
| JP | 2001-011342 A | 1/2001 |
| JP | 2003-73220 A | 3/2003 |
| JP | 2003-231614 A | 8/2003 |
| JP | 2004-175709 A | 6/2004 |
| JP | 2006-22008 A | 1/2006 |
| JP | 2007-153744 A | 6/2007 |
| JP | 2007-217320 A | 8/2007 |
| JP | 2008-231100 A | 10/2008 |
| KR | 10-2008-0095882 A | 10/2008 |
| WO | WO 2007/043555 A1 | 4/2007 |
| WO | WO 2007/083753 A1 | 7/2007 |
| WO | WO 2007/123115 A1 | 11/2007 |

OTHER PUBLICATIONS

Extended European Search Report dated Jun. 19, 2015, by the European Patent Office in corresponding European Application No. 10854693.8. (3 pages).

* cited by examiner

LIQUID COSMETIC

TECHNICAL FIELD

The present invention relates to a liquid cosmetic, more specifically to a liquid cosmetic which is suited to a liquid cosmetic applicator using a brush or a pen feed as an applying means and which has good water resistance and is excellent in an adhesive property to the skin.

BACKGROUND ART

Cosmetics prepared by dissolving dyes as a colorant in water, water-soluble organic solvents and the like and cosmetics prepared by dispersing pigments as a colorant in water, water-soluble organic solvents and the like with surfactants and water-soluble resins have so far been known as liquid cosmetics of a type in which they are used with being stored in an applicator.

The above conventional liquid cosmetics are unsatisfactory in water resistance when a dye is used. Also, when a pigment is used, water resistance is provided by adding a film-formable resin for fixing when a dispersant is a surfactant, or by the fixing property of a dispersant when a water-soluble resin is used for a dispersant.

However, conventional cosmetics prepared by using pigments for colorants and adding film-formable resins for fixing and cosmetics prepared by using water-soluble resins for dispersants bring about the problems that they are still unsatisfactory in water resistance and that the cosmetics are gradually lost when sweating.

The present applicants present liquid cosmetics of makeup cosmetics comprising an aqueous dispersion and liquid cosmetic applicators in which the above liquid cosmetics are stored (refer to, for example, patent documents 1 to 3). The liquid cosmetics and the like are excellent in an applying performance and provide satisfactory drawn lines, and they contain lecithin and nonionic surfactants in large amounts and have good performances in terms of being completely wiped off with a wet wiper as shown in a wiping test. On the other hand, they involve a little problem in terms of being inferior particularly in a water resistant fixing property.

Further, the present applicants present an eye liner liquid in which a pearl pigment is used as a liquid cosmetic suited to a brush and a liquid cosmetic applicator in which the liquid cosmetic is stored (refer to, for example, patent document 4). The cosmetic is an eye liner liquid providing a beautiful pearl color, wherein a viscosity at a shear rate is prescribed for stabilization of the eye liner liquid, and hydrogenated lecithin and polyethylene glycol fatty acid ester and the like as a dispersant are used for stabilization to make it possible to draw beautiful eye lines. Because of influences exerted by using large particles and adding 0.5% of the hydrogenated lecithin and 0.5% of the polyethylene glycol fatty acid ester for stabilization thereof, a little problem is involved therein in terms of being inferior in a water resistant fixing property.

On the other hand, known as a makeup liquid cosmetic for a pen type applicator are liquid cosmetics having a low viscosity comprising at least a pigment, water, a water-soluble polymer and a single component or a mixture of propylene glycol, 1,3-butylene glycol, glycerin and polyethylene glycol, wherein a copolymer of a hydrophobic unsaturated monomer and a hydrophilic unsaturated monomer and/or a salt thereof are used as the water-soluble polymer described above to control a viscosity to 1 to 50 cps (refer to, for example, patent document 5). In the above patent document, an eye liner prepared by using an ammonium salt of a methylstyrene-methacrylic acid copolymer is disclosed in Example 1; an eye shadow prepared by using a methoxyethylene-maleic anhydride copolymer is disclosed in Example 2; an eyebrow prepared by using an ammonium salt of a styrene-maleic anhydride copolymer is disclosed in Example 3; and an eye liner prepared by using a methyl methacrylate-methacrylic acid copolymer is disclosed in Example 5. Film-forming agents are not added to the liquid cosmetics, and they involve the problem that it is difficult to provide an adhesive property to the skin and water resistance.

Further, known are eye liners prepared by dispersing inorganic pigments with polyaspartic acid, polyglutamic acid and salts thereof and further blending polymer emulsions (refer to, for example, patent document 6) and eye liners filled in a pen type vessel which comprise black iron oxide, red iron oxide, Prussian blue, anionic dispersants and nonionic dispersants (refer to, for example, patent document 7). These cosmetics are good dispersions, but they are blended with anionic surfactants such as polyaspartic acid salts in large amounts and involve the problem that it is difficult to provide an adhesive property to the skin and water resistance.

Also, known as well are liquid cosmetics which comprise a pigment, a betaine type acrylic acid base amphoteric resin and a film-forming agent and which have a viscosity falling in a range of 1 to 300 mPa·s (refer to, for example, patent document 8), but the dispersant is limited to the betaine type resin, and the existing situation is that they involve the problem that they are not yet satisfactory in water resistance.

PRIOR ART DOCUMENTS

Patent Documents

Patent document 1: Japanese Patent Publication Hei 2 No. 12924 (claims, examples and others)
Patent document 2: Japanese Patent Publication Hei 4 No. 66447 (claims, examples and others)
Patent document 3: Japanese Patent Application Laid-Open Hei 10 No. 231233 (claims, examples and others)
Patent document 4: Japanese Patent Application Laid-Open No. 2000-247833 (claims, examples and others)
Patent document 5: Japanese Patent Publication Hei 7 No. 47529 (claims, examples and others)
Patent document 6: Japanese Patent Application Laid-Open No. 2004-175709 (claims, examples and others)
Patent document 7: Japanese Patent Application Laid-Open No. 2003-231614 (claims, examples and others)
Patent document 8: Japanese Patent Application Laid-Open No. 2003-73220 (claims, examples and others)

OUTLINE OF THE INVENTION

Problems to be Solved by the Invention

In light of the problems on the conventional arts and the existing situation each described above, the present invention intends to solve them, and an object thereof is to provide a liquid cosmetic which can be used for a liquid cosmetic applicator using a brush or a pen feed as an applying means and which is excellent in water resistance and an adhesive property to the skin when applied.

Means for Solving the Problems

In light of the conventional problems described above and the like, intense researches repeated by the present inventors have resulted in finding that the object described above is achieved by a liquid cosmetic stored in a liquid cosmetic applicator using a brush or a pen feed as an applying means, wherein the liquid cosmetic comprises at least a dispersant comprising a film-formable resin in an amount falling in a specific range, a film-forming agent and a surfactant in addition to carbon black and water, and a viscosity of the liquid cosmetic is controlled to a specific range. Thus, the present invention has come to be completed.

That is, the present invention comprises the following items (1) to (5).

(1) A liquid cosmetic stored in a liquid cosmetic applicator using a brush or a pen feed as an applying means, wherein the liquid cosmetic comprises at least carbon black, water, 0.5 to 5% by mass of a dispersant comprising a film-formable resin, 2 to 15% by mass (in terms of a solid content) of a film-forming agent and 0.5% by mass or less of a surfactant, and a viscosity thereof measured at a temperature of 25° C. and a shear rate of 3.83 $S^{-1}$ by means of an ELD type viscometer falls in a range of 2 to 8 mPa·s.

(2) The liquid cosmetic as described in the above item (1), wherein the dispersant comprising a film-formable resin is a copolymer made from the monomers comprising one or more kinds selected from acrylic acid, methacrylic acid, alkyl esters or derivatives thereof, vinyl acetate and vinylpyrrolidone.

(3) The liquid cosmetic as described in the above item (2), wherein the dispersant comprising a film-formable resin is a copolymer of at least one of acrylic acid, methacrylic acid or alkyl esters or derivatives thereof with vinyl acetate, a copolymer of vinylpyrrolidone with vinyl acetate or a copolymer of at least one of acrylic acid, methacrylic acid or alkyl esters thereof with octylacrylamide.

(4) The liquid cosmetic as described in any one of the above items (1) to (3), wherein the liquid cosmetic applicator is provided with a sliver type vessel in which the liquid cosmetic is held in a sliver or a collector type vessel in which the liquid cosmetic is held between leaf bodies.

(5) The liquid cosmetic as described in any one of the above items (1) to (4), wherein the liquid cosmetic is used for an eye liner or an eyebrow.

Effects of the Invention

According to the present invention, exerted is the specific effect that obtained is a liquid cosmetic which can be used for a liquid cosmetic applicator using a brush or a pen feed as an applying means, which is very excellent in a water resistant fixing property when applied and liable to draw fine lines and which is a black color base one using carbon black as a coloring material and has a low viscosity.

MODE FOR CARRYING OUT THE INVENTION

Figure 1:
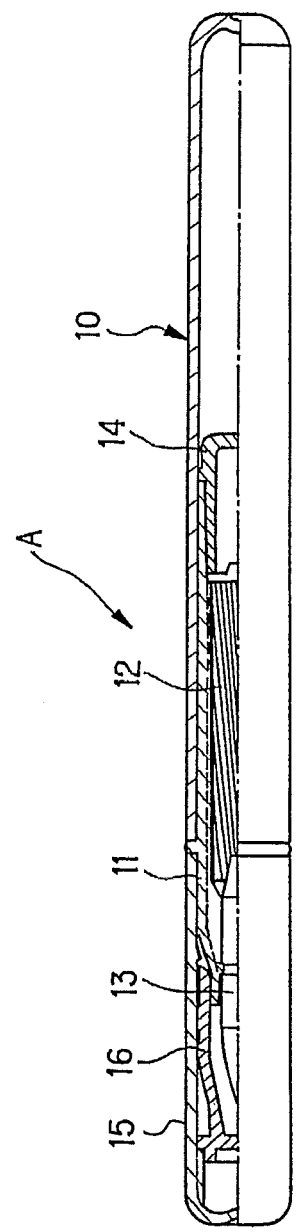
FIG. 1 is a partial cross section showing one example of the embodiment of the liquid cosmetic of the present invention.

The embodiments of the present invention shall be explained below in detail.

The liquid cosmetic of the present invention is characterized in that it is a liquid cosmetic stored in a liquid cosmetic applicator using a brush or a pen feed as an applying means, wherein the liquid cosmetic comprises at least carbon black, water, 0.5 to 5% by mass of a dispersant comprising a film-formable resin, 2 to 15% by mass (in terms of a solid content) of a film-forming agent and 0.5% by mass or less of a surfactant, and a viscosity thereof measured at a temperature of 25° C. and a shear rate of 3.83 $S^{-1}$ by means of an ELD type viscometer falls in a range of 2 to 8 mPa·s.

The carbon black used in the present invention is used as a coloring material and shall not specifically be restricted as long as it is carbon black usually used as a coloring material for black liquid cosmetics, and various carbon blacks can be used.

A content of the carbon black is preferably 1 to 20% by mass, more preferably 5 to 15% by mass based on the total amount of the liquid cosmetic. If a content of the carbon black is less than 1% by mass, the color is lightly developed and unsatisfactory for the cosmetic. On the other hand, if it exceeds 20% by mass, the viscosity is increased too much, and the liquid is not smoothly discharged by the liquid cosmetic applicator of a sliver type or a collector type used in the present invention, so that both ranges are not preferred.

The dispersant used in the present invention comprises a film-formable resin, and it enhances dispersibility of the carbon black which is a coloring material and functions as a resin for forming a film.

The dispersant which can be used shall not specifically be restricted as long as it has the function described above, and it includes, for example, copolymers made from monomers comprising one or more kinds selected from acrylic acid, methacrylic acid, alkyl esters or derivatives thereof, vinyl acetate and vinylpyrrolidone, and betaine type acrylic acid base amphoteric resins. It is preferably a copolymer of one selected from acrylic acid, methacrylic acid or alkyl esters or derivatives thereof with vinyl acetate, a copolymer of vinylpyrrolidone with vinyl acetate and a copolymer of at least one of acrylic acid, methacrylic acid or alkyl esters thereof with octylacrylamide in terms of further enhancing a dispersing performance of the carbon black, and it is particularly preferably a copolymer of at least one of acrylic acid, methacrylic acid or alkyl esters thereof with octylacrylamide in terms of further enhancing a dispersing performance and film-forming ability thereof.

A content of the dispersant is preferably 0.5 to 5% by mass, more preferably 2 to 4% by mass based on the total amount of the liquid cosmetic.

If a content of the dispersant is less than 0.5% by mass, dispersion stability of the carbon black which is a coloring material is unsatisfactory. On the other hand, if it is contained in an amount exceeding 5% by mass, the viscosity is increased too much, and the dispersion stability is not enhanced, so that it is not economical.

The film-forming agent used in the present invention includes, for example, emulsion resins of copolymers made from monomers comprising one or more kinds selected from acrylic acid, methacrylic acid, alkyl esters or derivatives thereof, styrene and vinyl acetate.

In the present invention, the film-forming agent described above comprises as well a film-formable resin, and it is different from the dispersant described above in terms of a soluble resin or an emulsion resin. The emulsion resin is an aqueous suspension obtained by subjecting monomers to emulsion polymerization in water as a polymerization solvent. In dispersion of the carbon black in the present invention, a more stable dispersion liquid of the carbon black is obtained by the soluble resin rather than the emulsion resin. They are used in distinction from each other in terms of the above point.

A content of the film-forming agent (emulsion resin) is preferably 2 to 15% by mass, more preferably 2 to 10% by mass in terms of a solid content (resin content) based on the total amount of the liquid cosmetic.

If a content of the film-forming agent (emulsion resin) is less than 2% by mass in terms of a solid content (resin content), the water resistant performance is deteriorated. On the other hand, if it is contained in an amount exceeding 15% by mass, an applying part (a brush, a pen feed and the like) of the liquid cosmetic applicator is dried to bring about the defect of being impossible to be applied in a certain case, and therefore it is not preferred.

A surfactant is used in a certain case for stabilizing the film-forming agent (emulsion resin), but the surfactant blended with such a film-forming agent exerts less influence on the fixing property in the present invention, so that it shall not be taken into consideration in terms of a content.

The surfactant used in the present invention is allowed to function as a dispersion auxiliary agent for dispersing the carbon black and includes, for example, nonionic surfactants, anionic surfactants and cationic surfactants, and it includes lecithin, propylene glycol fatty acid esters, glycerin fatty acid esters, polyglycerin fatty acid esters and in addition thereto, one kind or mixtures of two or more kinds of polyoxyethylene alkyl ethers, polyoxyethylene polyoxypropylene alkyl ethers, polyoxyethylene alkyl ether phosphate, polyethylene glycol fatty acid esters, alkylsulfates, sulfonates, polyoxyethylene alkyl ether sulfates and the like.

A content of the surfactants is preferably 0.5% by mass or less, more preferably 0 to 0.3% by mass based on the total amount of the liquid cosmetic.

If the surfactant is contained in an amount exceeding 0.5% by mass, the liquid cosmetic is inferior in water resistance and can not provide sufficiently high fixing strength, and therefore it is not preferred.

In the liquid cosmetic of the present invention, water (including refined water, distilled water, ion-exchanged water, purified water, ultra pure water and the like) is used as a solvent. A content of water is a balance obtained by deducting the amounts of the respective components described above and optional components described later from the total amount of the liquid cosmetic.

Further, optional components used for conventional liquid cosmetics in addition to the essential components described above may be contained in the liquid cosmetic of the present invention. To be specific, antiseptic agents, antioxidants, neutralizing agents, UV absorbers, chelating agents, moisturizers, beauty ingredients, fragrances, viscosity modifiers and the like can be contained in suitable amounts as long as the effects of the present invention are not damaged.

In the liquid cosmetic of the present invention, a viscosity thereof measured at a temperature of 25° C. and a shear rate of 3.83 $S^{-1}$ by means of an ELD type viscometer falls in a range of 2 to 8 mPa·s, particularly preferably 3 to 6 mPa·s.

If the viscosity value is less than 2 mPa·s, the liquid flows into wrinkles and the like to cause blurring. On the other hand, if it exceeds 8 mPa·s, the viscosity is high, and therefore the liquid is not smoothly discharged when the liquid cosmetic is stored in the liquid cosmetic applicator using a brush or a pen feed as an applying means in the present invention, so that it is not preferred. The above viscosity means a value measured under the following measuring conditions (including examples and the like described later), to be specific, measured at a temperature of 25° C. and a shear rate of 3.83 ($S^{-1}$) in 1 rpm of a standard cone rotor by means of an ELD type viscometer manufactured by Tokimec Inc.

In the present invention, the liquid cosmetic applicator using a brush or a pen feed as an applying means shall not specifically be restricted as long as it is a liquid cosmetic applicator equipped with a brush or a pen feed which is used for an eye liner or an eyebrow, and it includes preferably an applicator which is excellent in usability, convenience and an applying property and which is provided with a sliver type vessel holding a liquid cosmetic in a sliver or a collector type vessel holding a liquid cosmetic between leaf bodies.

The liquid cosmetic applicator of a sliver type includes, for example, an applicator having a structure in which, as shown in FIG. 1, an inner barrel 11 is provided in an applicator main body 10; an impregnation member 12 comprising a sliver and the like which is impregnated with a liquid cosmetic is accommodated in the above inner barrel 11; a pen feed 13 for applying the liquid cosmetic is provided at a tip side of the impregnation member 12; and a plug 14 is fixed at a rear end of the inner barrel 11. A member 15 is a cap having an inner cap part 16. The liquid cosmetic applicator A of the above embodiment is used by removing the cap 15.

Figure 2:
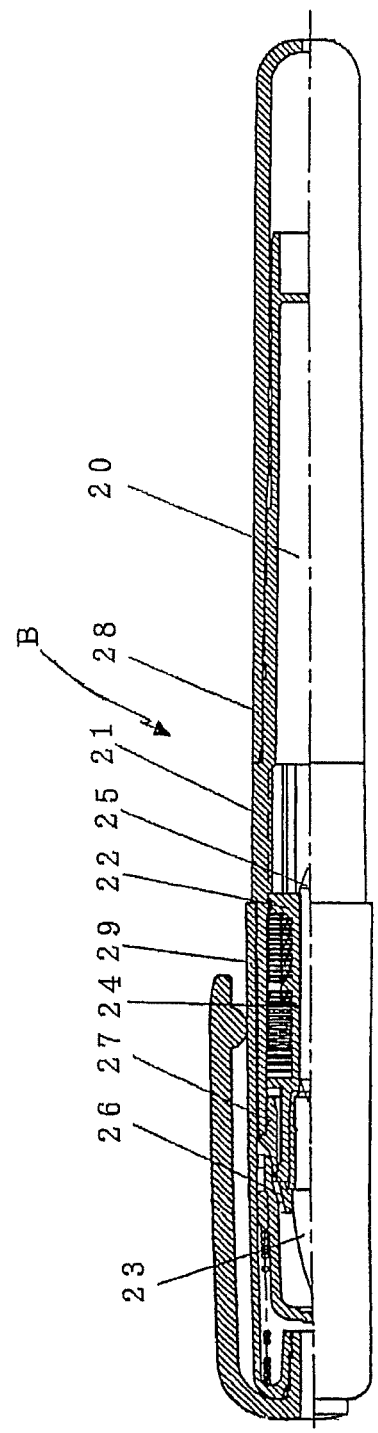
FIG. 2(a) is a partial cross section showing another example of the embodiment of the liquid cosmetic of the present invention.

The liquid cosmetic applicator of a collector type of a free liquid system includes, for example, an applicator in which, as shown in FIG. 2, a liquid cosmetic 20 is not occluded in a sliver and the like and in which it is filled in a barrel which is also a tank part 21 directly storing the liquid cosmetic. Provided is a constitution in which leaf bodies 22 (an ink holder, a collector member) for temporarily holding the liquid cosmetic 20 pushed out from the tank part 21 in order to prevent it from blobbing from a pen tip and an air hole when air in the tank part 21 is expanded by a rise in temperature is built in a front part of the tank part 21 and in which a pen tip (brush) 23 of a brush type as an applying member is provided in a tip part of the collector member 22.

The liquid cosmetic 20 is discharged from the tank part 21 to the pen tip 23 by delivering it via a feeder 25 having an ink passage 24 in a central hole of the collector member 22.

Members 26, 27 in FIG. 2 are holder members, and a member 28 is a rear holder fixed at a rear part of the tank part 21. A part 29 is a cap having an inner cap. Also, the liquid cosmetic may be discharged by arranging a rear part of the pen tip 23 directly in the tank part 21 without interposing the feeder 25 therebetween. The liquid cosmetic applicator B of the above embodiment is used by removing the cap 29.

The liquid cosmetic of the present invention thus constituted can be used for a liquid cosmetic applicator using a brush or a pen feed as an applying means, wherein the liquid cosmetic comprises at least carbon black, water, 0.5 to 5% by mass of a dispersant comprising a film-formable resin, 2 to 15% by mass (in terms of a solid content) of a film-forming agent and 0.5% by weight or less of a surfactant, and a viscosity thereof measured at a temperature of 25° C. and a shear rate of 3.83 $S^{-1}$ by means of an ELD type viscometer falls in a range of 2 to 8 mPa·s. Accordingly, exerted is the specific effect that obtained is a liquid cosmetic which is very excellent in a water resistant fixing property when applied and liable to draw fine lines, which is a black color base one using carbon black as a coloring material and has a low viscosity and which is suitable for use in an eye liner, an eyebrow or the like.

EXAMPLES

Next, the present invention shall be explained in further details with reference to examples and comparative examples, but the present invention shall not be restricted to the examples shown below.

Examples 1 to 7 and Comparative Examples 1 to 6

Liquid cosmetics (blending unit: % by mass, total amount: 100% by mass) having recipes shown in the following Table 1 and Table 2 were prepared to measure the viscosity values of the respective liquid cosmetics by the measuring method described above and evaluate a fixing property, an applying performance and liquid stability thereof according to the following evaluation method.

The results thereof are shown in the following Table 1 and Table 2.

Evaluation Method of Fixing Property:

The respective liquid cosmetics were filled in a cosmetic applicator of a brush pen type shown in FIG. 2, and the liquid cosmetic was applied on the back of a hand and dried for 10 minutes. Then, it was sprayed with flowing water and rubbed with the bulb of a finger to sensorially evaluate a removed degree of the applied cosmetic in a visual manner according to the following evaluation criteria.

Evaluation Criteria:
◎: very good (peeling in the applied part is not observed at all, very good)
○: good (less peeling in the applied part is observed, good)
Δ: average (peeling in the applied part is partially observed)
×: inferior (the applied part is almost peeled off)

Evaluation Method of Applying Performance:

The respective liquid cosmetics were filled in the cosmetic applicator of a brush pen type shown in FIG. 2, and five lines having a width of 1 to 2 mm and a length of about 5 cm were drawn on the back of a hand to sensorially evaluate a drawn state and drawn line intensity thereof according to the following evaluation criteria.

Evaluation criteria:
◎: drawn lines are deep and easy to draw
○: easy to draw and sufficiently deep
Δ: slight starving and blurring are observed, but judged to be within a practical area
×: starving and blurring are observed, and felt unsatisfactory Evaluation Method of Liquid Stability:

The respective liquid cosmetics which are the filled liquids were stored in a thermostatic bath of 50° C. for 1 month, and then a viscosity thereof was measured. It was compared with an initial viscosity value thereof to evaluate stability of the liquids according to the following evaluation criteria. Evaluation criteria:
○: difference from the initial value is ±1 (mPa·s) or less
Δ: difference from the initial value exceeds ±1 (mPa·s) and is ±2 (mPa·s) or less
×: difference from the initial value exceeds ±2 (mPa·s)

TABLE 1

| Components in composition | Specific compound name | Example 1 | 2 | 3 | 4 | 5 | 6 | 7 |
|---|---|---|---|---|---|---|---|---|
| Pigment | Carbon black | 10 | 10 | 10 | 10 | 10 | 10 | 10 |
| Dispersant | Vinyl acetate•vinylpyrrolidone copolymer | 0.8 | 0 | 4.5 | 0 | 4.5 | 0 | 0 |
| Dispersant | Vinylpyrrolidone dimethylaminopropylacrylamide copolymer | 0 | 3 | 0 | 3 | 0 | 0 | 0 |
| Dispersant | Octylacrylamide•acrylic ester copolymer | 0 | 0 | 0 | 0 | 0 | 3 | 0 |
| Dispersant | Betaine type acrylic acid base amphoteric resin (other resin) | 0 | 0 | 0 | 0 | 0 | 0 | 3 |
| Surfactant | Polyoxyethylene behenyl ether | 0 | 0 | 0 | 0.3 | 0 | 0 | 0 |
| Surfactant | Polyethylene glycol monostearate | 0 | 0 | 0 | 0 | 0.5 | 0 | 0 |
| Film-forming agent emulsion | Alkyl acrylate copolymer emulsion*1 | 20 | 15 | 10 | 15 | 10 | 15 | 15 |
| (resin content in emulsion) | | 10 | 7.5 | 5 | 6.75 | 4.5 | 7.5 | 6.75 |
| Neutralizer | Aminomethylpropanol | 0.1 | 0.3 | 0.5 | 0.3 | 0.5 | 0.3 | 0.3 |
| Chelating agent | Disodium edetate | 0.3 | 0.3 | 0.3 | 0.3 | 0.3 | 0.3 | 0.3 |
| Moisturizing agent | 1,3-butylene glycol | 8 | 8 | 8 | 8 | 8 | 8 | 8 |
| Antiseptic agent | Methylparaben | 0.4 | 0.4 | 0.4 | 0.4 | 0.4 | 0.4 | 0.4 |
| Antiseptic agent | Sodium dehydroacetate | 0.1 | 0.1 | 0.1 | 0.1 | 0.1 | 0.1 | 0.1 |
| Refined water | Refined water | balance | balance | balance | balance | balance | balance | balance |
| Viscosity (mPa · s) | Shear rate: 3.83 ($S^{-1}$) | 6 | 5 | 6 | 4 | 4 | 3 | 7 |
| Fixing property | | ○ | ◎ | ◎ | ○ | ○ | ◎ | Δ |
| Applying performance | | ◎ | ○ | ◎ | ○ | ◎ | ◎ | ○ |
| Liquid stability | | ○ | ○ | ○ | ○ | ○ | ○ | Δ |

*1 copolymer emulsion comprising two or more components of acrylic acid, methacrylic acid or alkyl (C1 to C4 and C8) esters thereof

TABLE 2

| Components in composition | Specific compound name | Comparative Example 1 | 2 | 3 | 4 | 5 | 6 |
|---|---|---|---|---|---|---|---|
| Pigment | Carbon black | 10 | 10 | 10 | 10 | 10 | 10 |
| Dispersant | Vinyl acetate•vinylpyrrolidone copolymer | 6 | 0.3 | 0 | 0 | 3 | 3 |
| Dispersant | Vinylpyrrolidone dimethylaminopropylacrylamide copolymer | 0 | 0 | 3 | 3 | 0 | 0 |
| Surfactant | Polyoxyethylene behenyl ether | 0 | 0 | 0 | 0 | 1 | 0 |
| Surfactant | Polyethylene glycol monostearate | 0 | 0 | 0 | 0 | 0.3 | 0.5 |
| Film-forming agent emulsion | Alkyl acrylate copolymer emulsion*1 | 20 | 20 | 32 | 0 | 15 | 15 |
| (resin content in emulsion) | | 10 | 10 | 16 | 0 | 6.75 | 6.75 |
| Neutralizer | Aminomethylpropanol | 0.5 | 0.05 | 0.3 | 0.3 | 0.3 | 0.3 |
| Chelating agent | Disodium edetate | 0.3 | 0.3 | 0.3 | 0.3 | 0.3 | 0.3 |
| Moisturizing agent | 1,3-butylene glycol | 8 | 8 | 8 | 8 | 8 | 8 |
| Antiseptic agent | Methylparaben | 0.4 | 0.4 | 0.4 | 0.4 | 0.4 | 0.4 |
| Antiseptic agent | Sodium dehydroacetate | 0.1 | 0.1 | 0.1 | 0.1 | 0.1 | 0.1 |
| Viscosity controller | Xanthan gum | 0 | 0 | 0 | 0 | 0 | 0.1 |
| Refined water | Refined water | balance | balance | balance | balance | balance | balance |
| Viscosity (mPa · s) | Shear rate: 3.83 (S$^{-1}$) | 9 | 5 | 6 | 4 | 4 | 11 |
| Fixing property | | ○ | X | ○ | X | X | ○ |
| Applying performance | | X | ○ | X | Δ | ○ | X |
| Liquid stability | | ○ | X | Δ | ○ | ○ | ○ |

*1copolymer emulsion comprising two or more components of acrylic acid, methacrylic acid or alkyl (C1 to C4 and C8) esters thereof As apparent from the results shown in the Table 1 and Table 2 described above, it has become clear that the liquid cosmetics prepared in Examples 1 to 7 falling in the scope of the present invention are excellent in a fixing property, an applying performance and liquid stability thereof as compared with those prepared in Comparative Examples 1 to 6 falling outside the scope of the present invention.

To observe individually the comparative examples, in Comparative Examples 1 and 2, a content of the dispersant comprising a film-formable resin falls outside the range of the present invention (exceeding the upper limit or below the lower limit); in Comparative Examples 3 and 4, a content of the film-forming agent falls outside the range of the present invention (exceeding the upper limit or below the lower limit); in Comparative Example 5, a content of the surfactant falls outside the range of the present invention (exceeding the upper limit); and in Comparative Example 6, the viscosity measured at a temperature of 25° C. and a shear rate of 3.83 S$^{-1}$ by means of an ELD type viscometer falls outside the range of the present invention. It has become clear that the effects of the present invention can not be exerted in the above cases.

INDUSTRIAL APPLICABILITY

Obtained is a liquid cosmetic stored in a liquid cosmetic applicator using a brush or a pen feed as an applying means and suited for use in an eyeliner or an eyebrow.

LIST OF REFERENCE LETTERS AND NUMERALS

A Liquid cosmetic applicator
10 Applicator main body

What is claimed is:

1. A liquid cosmetic for an eyeliner or for applying to an eyebrow stored in a liquid cosmetic applicator using a brush or a pen feed as an applying means, wherein the liquid cosmetic comprises at least carbon black, water, 0.5 to 5% by mass of a dispersant comprising a soluble copolymer which is a copolymer of vinylpyrrolidone-vinyl acetate, a copolymer of vinylpyrrolidone-dimethylaminopropylacrylamide, or a copolymer of octylacrylamide-acrylic ester, 2 to 15% by mass, in terms of a solid content, of a film-forming agent of an emulsion of a water-insoluble copolymer made from two or more components selected from acrylic acid, methacrylic acid, alkyl (C1 to C4 and C8) esters of acrylic acid, or alkyl (C1 to C4 and C8) esters of methacrylic acid, and 0.5% by mass or less of a surfactant, and a viscosity of the liquid cosmetic measured at a temperature of 25° C. and a shear rate of 3.83 S$^{-1}$ by means of an ELD type viscometer using a cone rotor falls in a range of 2 to 6 mPa·s.

2. The liquid cosmetic as described in claim 1, wherein the liquid cosmetic is stored in the liquid cosmetic applicator in which the liquid cosmetic is held in a sliver, or in which the liquid cosmetic is held between leaf bodies.

* * * * *